United States Patent [19]

Rosenblum et al.

[11] Patent Number: 5,624,827
[45] Date of Patent: Apr. 29, 1997

[54] DNA SEQUENCES ENCODING THE PLANT TOXIN GELONIN

[75] Inventors: Michael G. Rosenblum, Houston; Kenneth L. Beattie, The Woodlands, both of Tex.

[73] Assignee: Research Development Foundation, Carson City, Nev.

[21] Appl. No.: 327,440

[22] Filed: Oct. 21, 1994

Related U.S. Application Data

[63] Continuation of Ser. No. 755,949, Sep. 6, 1991, abandoned.
[51] Int. Cl.$^6$ .................... C12P 19/34; C12P 21/02; C12N 15/63; C07H 21/04
[52] U.S. Cl. .................. 435/91.5; 435/69.1; 435/243; 435/320.1; 435/348; 435/325; 435/354; 435/362; 435/366; 435/419; 435/252.33; 435/252.34; 435/252.35; 435/252.31; 435/254.2; 536/23.6
[58] Field of Search ................ 435/91.1, 172.3, 435/320.1, 91.5, 69.1, 240.1, 243; 536/23.1, 23.6; 935/16, 17, 23, 24

[56] References Cited

PUBLICATIONS

Shatzman, et al., Expression, Identification, and Characterization of Recombinant Gene Products in *Escherichia coli*, Methods in Enzymology, vol. 152, 1987, pp. 661–673.
Brinkman et al., B3(Fv)–PE38KDEL, a single–chain immunotoxin that causes complete regression of a human carcinoma in mice, Proc. Natl. Acad. Sci. USA, vol. 88, pp. 8616–8620, Oct. 1991.
Montanaro et al., A Metalloproteinase Associated with Gelonin, A Ribosome Inactivating Protein, Ital. J. Biochem., 1984, pp. 1–10.
Hostomský et al. (1987) Nucleic Acids Res. 15:4849–4856.
Aota, S. et al. (1987) Nucleic Acids Res. 165:r315–r391.
Chaudhary, V.K. et al. (1989) Nature 339: 394–397.
Montecucchi et al (1989) Int. J. Peptide Protein Res. 33: 263–267.
Young et al (1983) Proc. Nat. Acad. Sci. USA, 80: 1194–1198.
Falasco et al (1982) Biochem J. 207:505–509.
Stirpe F. et al. (1980) J. Biol. Chem 255:6947–6953.
Wosnick, M.A. et al (1987) Gene 60:115–127.
Berger, S.L. et al (1987) Methods in Enzymology 152 "Guide to Molecular Cloning Techniques" New York: Academic Press.
Sambrook, J et al. (1989) Molecular Cloning: A Laboratory Manual Cold Spring Harbor Press.

*Primary Examiner*—David Guzo
*Assistant Examiner*—Robert Schwartzman
*Attorney, Agent, or Firm*—Benjamin Aaron Adler

[57] ABSTRACT

The present invention provides the nucleotide sequence for a synthetic gene for the plant toxin gelonin and a process for producing, cloning and expressing this synthetic gene. The DNA sequence for a synthetic gene for gelonin as shown in sequence ID NO. 1. The present invention also provides expression vectors containing the DNA sequences for gelonin and cells transformed with these vectors. In addition, an immunotoxin comprising an antibody of conjugated to the protein gelonin.

33 Claims, 5 Drawing Sheets

SUPPORT-BOUND OLIGONUCLEOTIDE (1) ADD NEXT OLIGONUCLEOTIDE AND HYBRIDIZE

(2) WASH AWAY UNBOUND OLIGONUCLEOTIDE (3) CARRY OUT STEPWISE HYBRIDIZATION/WASHING UNTIL DESIRED GENE IS ASSEMBLED (1) SEAL NICKS WITH DNA LIGASE (2) RELEASE FROM SUPPORT (EcoRI)

LIGATE ASSEMBLED GENE INTO VECTOR

NAME OF GENE: GELONIN

| # | oligo name | length | SEQUENCE (5'→3') |
|---|---|---|---|
| 1. | Btgel1 | 45+bt | Bt-TTTCGACGGTCGCACGCTGCGGAATTCAGCATATGGGTCTGGATA |
| 2. | Btgel2 | 61+bt | Bt-TTTCGACGGTCGCACGCTGCGTCTAGAAGCTTCACTATTCCGGGTCTTTGTCCACGAATTT |
| 3. | gel1 | 40+p | p-CCGTTAGCTTCAGCACCAAAGGCGCGACCTACATCACCTA |
| 4. | gel2 | 40+p | p-CGTTAACTTCCTGAACGAACTGCGTGTTAAACTGAAACCG |
| 5. | gel3 | 40+p | p-GAAGGTAACAGCCATGGCATCCCGCTGCTGCGTAAAGGTG |
| 6. | gel4 | 40+p | p-ATGACCCGGGTAAATGCTTCGTGCTGGTGGCGCTGAGCAA |
| 7. | gel5 | 40+p | p-CGATAACGGTCAGCTGGCAGAAATCGCAATCGATGTTACC |
| 8. | gel6 | 40+p | p-AGCGTGTACGTAGTTGGCTATCAGGTGCGTAACCGCAGCT |
| 9. | gel7 | 40+p | p-ACTTCTTCAAAGATGCTCCGGATGCAGCGTACGAAGGCCT |
| 10. | gel8 | 40+p | p-GTTCAAAAACACCATCAAAAACCCGCTGCTGTTCGGTGGC |
| 11. | gel9 | 40+p | p-AAAACTCGTCTGCACTTCGGTGGCAGCTATCCGAGCCTGG |
| 12. | gel10 | 40+p | p-AAGGCGAAAAAGCGTACCGCGAAACTACCGATCTGGGTAT |
| 13. | gel11 | 40+p | p-CGAACCGCTGCGCATCGGCATCAAAAAACTGGACGAAAAC |
| 14. | gel12 | 40+p | p-GCGATCGACAACTACAAACCGACCGAAATCGCGAGCTCTC |
| 15. | gel13 | 40+p | p-TGCTGGTTGTGATCCAGATGGTGAGCGAAGCGGCACGTTT |
| 16. | gel14 | 40+p | p-CACCTTCATCGAAAACCAGATTCGTAACAACTTCCAGCAG |
| 17. | gel15 | 40+p | p-CGTATCCGTCCGGCGAACAACACCATCTCTCTGGAAAACA |
| 18. | gel16 | 40+p | p-AATGGGGCAAACTGAGCTTCCAGATCCGTACCAGCGGTGC |
| 19. | gel17 | 40+p | p-GAACGGTATGTTCAGCGAAGCGGTGGAACTGGAACGCGCG |
| 20. | gel18 | 40+p | p-AACGGCAAAAAATACTACGTGACTGCGGTGGATCAGGTGA |
| 21. | gel19 | 40+p | p-AACCGAAAATCGCACTGCTGAAATTCGTGGACAAAGACCC |
| 22. | gel20 | 30+p | p-GGAATAGTGAAGCTTCTAGACGCAGCGTGC |
| 23. | gel21 | 40+p | p-CAGCAGTGCGATTTTCGGTTTCACCTGATCCACCGCAGTC |
| 24. | gel22 | 40+p | p-ACGTAGTATTTTTTGCCGTTCGCGCGTTCCAGTTCCACCG |
| 25. | gel23 | 40+p | p-CTTCGCTGAACATACCGTTCGCACCGCTGGTACGGATCTG |
| 26. | gel24 | 40+p | p-GAAGCTCAGTTTGCCCCATTTGTTTTCCAGAGAGATGGTG |
| 27. | gel25 | 40+p | p-TTGTTCGCCGGACGGATACGCTGCTGGAAGTTGTTACGAA |
| 28. | gel26 | 40+p | p-TCTGGTTTTCGATGAAGGTGAAACGTGCCGCTTCGCTCAC |
| 29. | gel27 | 40+p | p-CATCTGGATCACAACCAGCAGAGAGCTCGCGATTTCGGTC |
| 30. | gel28 | 40+p | p-GGTTTGTAGTTGTCGATCGCGTTTTCGTCCAGTTTTTTGA |
| 31. | gel29 | 40+p | p-TGCCGATGCGCAGCGGTTCGATACCCAGATCGGTAGTTTC |
| 32. | gel30 | 40+p | p-GCGGTACGCTTTTTTCGCCTTCCAGGCTCGGATAGCTGCCA |
| 33. | gel31 | 40+p | p-CCGAAGTGCAGACGAGTTTTGCCACCGAACAGCAGCGGGT |
| 34. | gel32 | 40+p | p-TTTTGATGGTGTTTTTGAACAGGCCTTCGTACGCTGCATC |
| 35. | gel33 | 40+p | p-CGGAGCATCTTTGAAGAAGTAGCTGCGGTTACGCACCTGA |
| 36. | gel34 | 40+p | p-TAGCCAACTACGTACACGCTGGTAACATCGATTGCGATTT |
| 37. | gel35 | 40+p | p-CTGCCAGCTGACCGTTATCGTTGCTCAGCGCCACCAGCAC |
| 38. | gel36 | 40+p | p-GAAGCATTTACCCGGGTCATCACCTTTACGCAGCAGCGGG |
| 39. | gel37 | 40+p | p-ATGCCATGGCTGTTACCTTCCGGTTTCAGTTTAACACGCA |
| 40. | gel38 | 40+p | p-GTTCGTTCAGGAAGTTAACGTAGGTGATGTAGGTCGCGCC |
| 41. | gel39 | 54+p | p-TTTGGTGCTGAAGCTAACGGTATCCAGACCCATATGCTGAATTCCGCAGCGTGC |

DNA SEQUENCES ENCODING THE PLANT TOXIN GELONIN

This is a continuation of application Ser. No. 07/755,949, filed on Sep. 6, 1991, now abandoned.

BACKGROUND OF THE INVENTION

1. Field of the Invention

This invention relates generally to the immunotoxin gelonin and, more specifically, to the molecular biology of gelonin, including a process of a synthetic gene for gelonin.

2. Description of the Related Art

One current interest in cytotoxic substances involves their potential use to specifically target tumor cells. The plant toxin gelonin has received such consideration. Gelonin is a glycoprotein (M.W. approximately 29–30,000 Kd) purified from the seeds of *Gelonium multiforum*. Gelonin belongs to a class of potent ribosomal-inactivating plant toxins. Other members of this class of ribosomal-inactivating plant toxins are the chains of abrin, ricin and modeccin. Gelonin, like abrin and ricin, inhibits protein synthesis by damaging the 60S sub-unit of mammalian ribosomes. Although the A chain of ricin (RTA) has been popular for use in immunotoxins, gelonin appears to be more stable to chemical and physical treatment than RTA (Barbibieri et al., *Cancer Surv.* 1:489–520 (1982)). Furthermore, gelonin itself does not bind to cells and therefore is non-toxic (except in high concentrations) and is safe to manipulate in the laboratory. The inactivation of ribosomes is irreversible, does not appear to involve co-factors and occurs with an efficiency which suggests that gelonin acts enzymatically.

Gelonin and ricin are among the most active toxins which inhibit protein synthesis on a protein weight basis. Gelonin is 10 to 1000 times more active in inhibiting protein synthesis than ricin A chain. Peptides like ricin and abrin are composed of two chains, a A chain which is the toxic unit and a B chain in which acts by binding to cells. Unlike ricin and abrin, gelonin is composed of a single chain, and, because it lacks a B chain for binding to cells, it is itself relatively non-toxic to intact cells (Stirpe, et al. *J. Biol. Chem.* 255:6947–6953 (1980)). Mammalian cells apparently lack the ability to bind and/or to internalize the native gelonin molecule. Conjugates of gelonin with a tumor-targeting monoclonal antibody, such as the monoclonal antibody ZME directed to an antigen present on certain tumor cells such as melanoma cells, provide both a specific method for binding the gelonin to the cell and a route for internalization of the gelonin antibody complex. One of the advantages of using the toxin gelonin over using toxins such as ricin A chain is this reduced toxicity to normal tissues as compared to the ricin A chain. Gelonin-coupled with a monoclonal antibody directed to an anti-tumor associated antigen is an active and selective immunotoxic agent for tumor therapy.

Several investigators have utilized gelonin as a cytotoxic agent chemically attached to monoclonal antibodies or to peptide hormone cellular targeting ligands. However, chemical modification of gelonin and cellular targeting moieties can reduce targeting efficiently and cytotoxic potential of gelonin itself. Furthermore, natural sources of gelonin are subject to variability in harvesting and plant growth which can affect gelonin cytotoxic activity. The ability to produce a synthetic gelonin toxin, chemically or utilizing recombinant technology, provides a plentiful, reproducible source of the toxin. Therefore, it is highly desirable to prepare a synthetic gene for gelonin and methods for preparation of the synthetic gene using recombinant technology.

SUMMARY OF THE INVENTION

The present invention provides the nucleotide sequence for a synthetic gene for gelonin and methods for its preparation. The DNA sequence for a synthetic gene for gelonin is shown in SEQ ID NO:1. The present invention also provides expression vectors containing these DNA sequences and cells transformed with these vectors.

According to one embodiment of the present invention, there is provided a method for producing, cloning and expressing a synthetic gene encoding gelonin. Initially, a double-stranded DNA fragment encoding the primary amino acid sequence determined from purified gelonin protein was designed. This DNA fragment was manipulated to facilitate synthesis, cloning, expression or biochemical manipulation of the gene. Next, a set of synthetic oligonucleotides capable of being linked together to assemble the desired gene was designed, synthesized, purified and 5'-phosphorylated. Subsequently, these oligonucleotides were annealed and ligated together to assemble the intact gene. The synthetic gene was ligated together with a suitable cloning vector and then the nucleotide sequence of the cloned gene was determined. After site directed mutagenesis was conducted to correct any undesired mutations in the cloned gene, the gene is subcloned into a suitable expression vector. The expression vector bearing the synthetic gelonin gene was inserted into a suitable expression host. Thereafter the expression host is maintained under conditions suitable for production of the gelonin gene product and gelonin protein is isolated and purified from cells expressing the gene.

According to another embodiment of the present invention, there is provided a synthetic DNA containing the sequence of nucleotides and fragments and derivatives thereof, coding for protein gelonin or for a polypeptide which inhibits cellular protein synthesis but does not bind a cell surface receptor, with the nucleotide sequence having the formula of Sequence ID NO. 1. Also provided is an expression vector containing synthetic gelonin DNA and host cells containing and expressing the synthetic gelonin gene.

According to yet another embodiment of the present invention, there is provided an immunotoxin comprising an antibody conjugated to the plant toxin protein gelonin.

For the purposes of the present invention, the term "fragment" is defined as any portion of SEQ ID No. 1 that would produce a protein that inhibits cellular protein synthesis but does not bind to a surface receptor. "Derivative" is defined as having the substitution of one or more individual nucleic acids such that the same protein or polypeptide is produced.

The present invention recognizes and addresses the previously mentioned long felt needs and provides a satisfactory meeting of those needs and its various embodiments. To one of skill in this art who has the benefit of this invention's teachings and disclosures, other and further objects and advantages will be clear, as well as others inherent therein. In conjunction with the accompanying drawings, the following description of presently preferred embodiments are given for the purpose of disclosure. Although these descriptions are detailed to insure adequacy and aid understanding, this is not intended to prejudice the purpose of a patent which is to claim an invention no matter how others may later disguise it by variations and form or additions of further improvements.

BRIEF DESCRIPTION OF THE DRAWINGS

So that the manner in which the above recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of this specification. It is to be noted, however, that the appended drawings illustrate preferred embodiments of the invention and therefore are not to be considered limiting of its scope. The invention may admit to other equally effective equivalent embodiments.

FIG. 5 depicts the oligonucleotide sequences used to assemble the gelonin gene.

DETAILED DESCRIPTION OF THE INVENTION

Recent developments in molecular biology have enabled the cloning, expressing and genetic engineering of numerous genes encoding proteins of biomedical and agricultural importance. A significant recent advance in this field is the capability to design and produce synthetic genes. The synthetic genes can encode proteins of known amino acid sequence, as well as novel proteins not existing in nature. This is particularly useful in the case of proteins of therapeutic value, such as gelonin. It is feasible to design, synthesize, clone and express a gene based on the amino acid sequence of a protein. The design, sequence, cloning, and expression are also possible even if specific information about the natural gene is unavailable, for example, if the gene has not yet been cloned. Furthermore, gene synthesis facilitates the engineering of variant gene products, possessing properties not found in the naturally occurring protein. For example, a gene encoding a protein normally found only in plants or animals can be designed, synthesized, and cloned into a vector which can yield large quantities of the protein in microbial hosts cells.

One advantage of synthetic genes is related to the redundancy of the genetic code. Most amino acids can be encoded by more than one three-base "codon" within a gene. Different organisms tend to employ different sets of codons for their proteins (S. Aota et al., Nucleic Acids Res., v. 16, Supplement, pp. r315–r391 (1987). In other words, the codons that are "preferred" by one organism are different from those preferred by another organism. This phenomenon is believed to be related to differences in the relative abundance of specific iso-accepting transfer RNA molecules for a given amino acid. Synthetic genes can be designed to incorporate preferred codons for a given expression system, even if the gene product is from a "heterologous" host organism, which employs a different set of preferred codons for some amino acids. It has been shown that synthetic genes encoding mammalian proteins can yield significantly greater protein product in a microbial host if the codons chosen in the gene design correspond to those most commonly used by the microbial host. This phenomenon was considered in the design of the gelonin gene (originally from plants) intended for introduction into the *Escherichia coli* expression host. For expression in a different host system the gelonin gene could be easily redesigned by one having ordinary skill in this art to incorporate codons optimal for the different host.

Another advantage of synthetic genes, actually enabled by the redundancy of the genetic code in this case, is that the DNA sequence encoding the gene of interest can be modified (without changing the amino acid sequence encoded) to contain a maximum number of uniquely occurring restriction enzyme recognition sites across the gene. The existence of numerous single-cutting restriction sites along a gene greatly facilitates the biochemical manipulation of the gene. For example, the ability to cleave out a segment of a gene and replace it with a different DNA sequence (enabled by closely spaced unique restriction sites) facilitates the introduction of new genetic information into the gene by recombinant DNA techniques. Useful manipulations enabled by this approach include introduction of mutations into defined regions of a gene, correction of mutations arising during gene synthesis, assembly and cloning, and creation of chimeric or fusion genes encoding proteins that combine functional domains of separate proteins.

The design of a synthetic gene can also accommodate non-coding "flanking" DNA sequences which can facilitate cloning and expression of the gene. For example, restriction endonuclease recognition sequences can be incorporated into flanking regions of the gene to enable the specific ligation of the gene into the desired cloning vector. Additionally, genetic signals can be incorporated into a synthetic gene which serve to control gene expression in vivo.

In addition, the de novo gene design can enable the in vivo targeting of a gene product to a certain tissue or organelle, which can enhance the therapeutic action of the gene product. For example, it is feasible to target a therapeutic agent to a particular cell type by incorporating into the relevant gene a sequence which encodes a polypeptide domain that specifically binds to a receptor on the surface of target cells.

Synthetic gene design can furthermore include considerations that are related to the chemical synthesis of short DNA strands and the assembly of oligonucleotides into longer duplex DNA segments. It is advantageous in the chemical synthesis of DNA to avoid the poor coupling efficiency associated with consecutive addition of numerous G or C residues to a chain. Also, it is desirable to avoid DNA sequences that contain intrastrand secondary structure (hairpin structure) or intermolecular complementarity, which can interfere with correct assembly of a gene during the annealing of component oligonucleotides. These objectives can usually be achieved by choosing alternative codons in the gene design.

The process of gene assembly comprises the following steps. First, the nucleotide sequence corresponding to the two strands of the desired coding region are written out, providing for perfect complementary base pairing between the two strands. Then any desired flanking sequences are added. For example, flanking sequences can be added to incorporate restriction endonuclease recognition sites adjacent to the coding sequence. The gene is then divided into overlapping sets of single-stranded fragments. The single-stranded fragments are chemically synthesized by automated DNA synthesis instruments. The extent of complementary overlap between successive oligonucleotides along the synthetic gene is a matter of choice, but is typically 6–20 bases. After all of the oligonucleotides needed for the synthetic gene have been chemically synthesized, they are preferably purified by polyacrylamide gel electrophoresis or high performance liquid chromatography. The purified oligonucleotides are then 5'-phosphorylated by the action of polynucleotide kinase and adenosine 5'-triphosphate. The strands are then annealed together, either in a single mixture, in blocks of 3–10 overlapping oligonucleotides, or by stepwise addition of oligonucleotides on a solid phase support. The ends of the assembled gene are provided with restriction sites which are employed in cloning of the gene. The assembled gene is typically cloned initially into the single-stranded vector M13 for convenient DNA sequencing. If necessary, mutations are corrected by oligonucleotide-directed mutagenesis.

Desired features of the synthetic gene (optimal codon usage, occurrence of unique restriction sites, elimination of secondary structure, etc.) can be designed with the assistance of any of several commercially available DNA sequence analysis programs for microcomputers.

Figure 1:
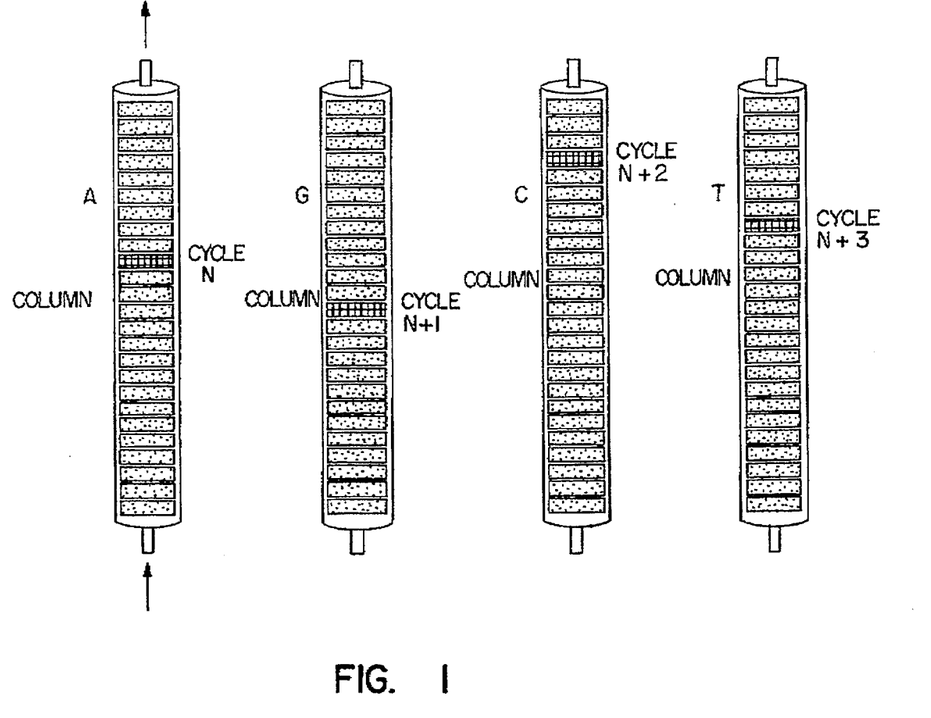
FIG. 1 depicts the schematic illustration of a process for chemically synthesizing oligonucleotides.

Two recent developments, both utilized in the instant invention, enable genes to be synthesized more rapidly and economically and create new opportunities for protein engineering (K. L. Beattie et al., Biotechnol. Appl. Biochem., 10, 510–521 (1988); K. L. Beattie and R. F. Fowler, Nature, 352, 548–549 (1991)). The first development, illustrated in FIG. 1, is a technology for rapid, economical synthesis of large numbers of oligonucleotides. This technology enables the preparation of all of the synthetic DNA needed for assembly of a gene in a single day. Referring to FIG. 1, nucleoside-derivatized controlled pore glass is placed within individual synthesis wafers, consisting of Teflon cylinders with porous ends to allow fluid flow through a stack of the wavers. Simultaneous addition of A, G, C or T to DNA chains attached to the CPG and retained within the wafers is accomplished by the sequential flow of reagents through the columns by the phosphoramidite method (L. J. McBride and M. H. Caruthers, Tetrahedron Lett., 24, 245–248 (1983)). After completion of each chemical reaction cycle, the wafers are sorted into different columns to provide for synthesis of a different nucleotide sequence within each wafer. The sequential position of one wafer (darkened) through four cycles is depicted, which would result in the addition of AGCT to the growing DNA chain contained therein.

Figure 2:
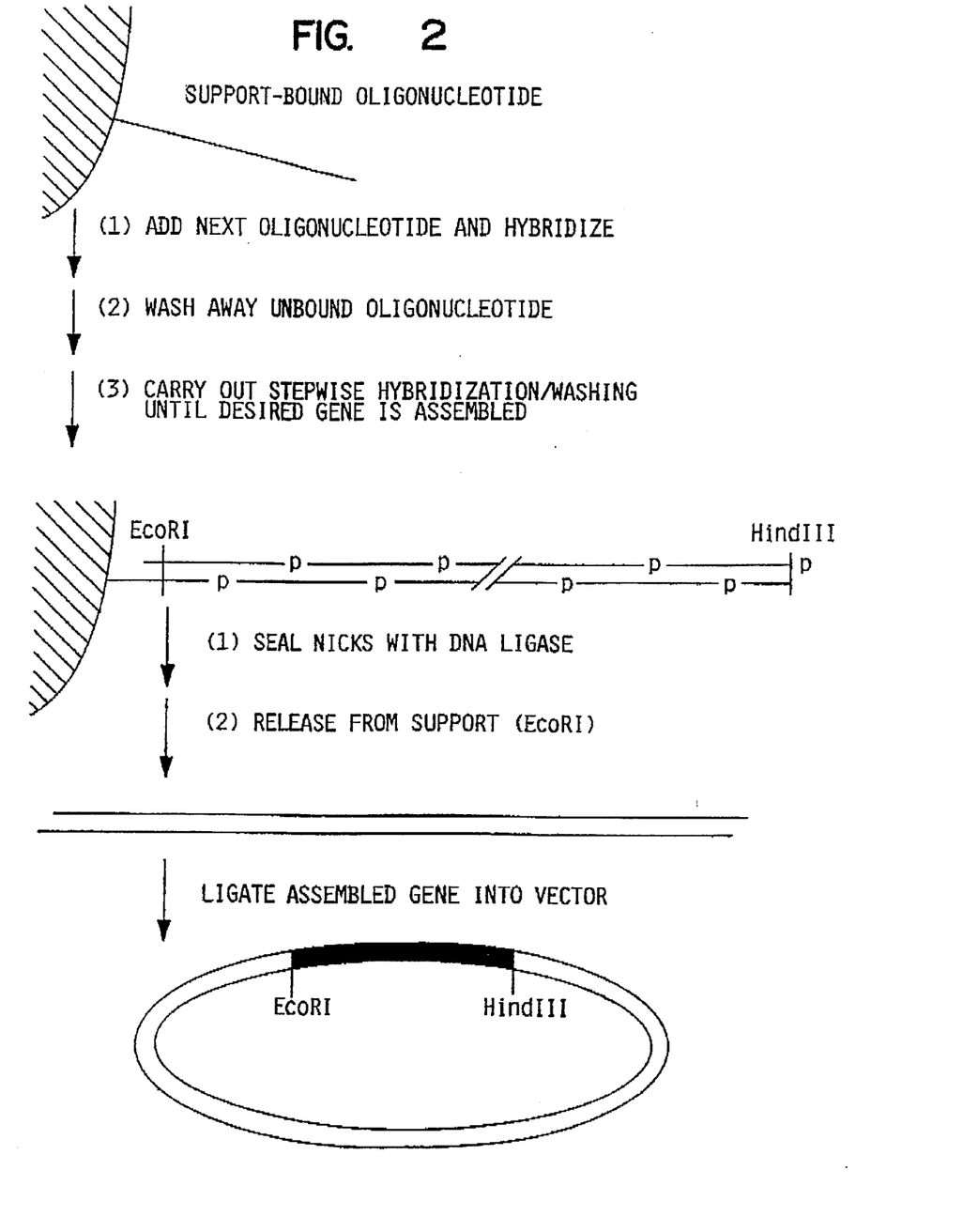
FIG. 2 shows an illustration of the solid phase gene assembly process.

A second technology development which facilitates gene synthesis provides a means for stepwise joining of synthetic oligonucleotides on a solid phase support to form a gene. Referring to FIG. 2, the desired gene is designed to be assembled from a set of overlapping complementary oligonucleotides. Assembly is initiated with an oligonucleotide bound at one end to a solid phase support. 5'-phosphorylated oligonucleotides are added sequentially (at molar excess) to the support-bound strand. At each step of the gene assembly unbound DNA is washed away before the next annealing reaction is performed. The completed assembly is treated with DNA ligase to seal the nicks, then the gene is released from the support by cleavage at a unique restriction site contained within the support-bound oligonucleotide. The released DNA is ligated into a suitable vector for sequencing and expression.

Numerous options exist for vector-host environments in the expression of the synthetic gene resulting in production of the encoded protein. These are discussed in detail in Methods in Enzymology, Vol. 152, 1987, Academic Press. Briefly, specialized expression vectors are available for insertion into bacterial, fungal, animal or plant hosts. The bacterium *Escherichia coli* is most commonly used for expression of "foreign" genes. The yeast *Saccharomvces cerevisiae* is another popular expression host. As mentioned previously, if the cloned gene of interest is chemically synthesized, optimal codon usage for the desired expression host is provided for in the gene design to increase the level of expression. Most expression vectors contain genetic control elements positioned adjacent to the cloning site which drive high levels of gene expression. Inducible promoters of expression vectors are typically derived from bacteria (e.g., tac, trp) or viruses (e.g., lambda, SV40). "Signal sequence" elements are sometimes included in the vector, to direct transport of the gene product out of the host cell. The signal sequence elements can facilitate purification and reduce proteolytic degradation. In the case of synthetic genes any desired genetic control element can be included within the duplex DNA being assembled. Some expression vectors contain a coding sequence immediately adjacent to the cloning site, such that in-frame insertion of the foreign coding sequence results in production of a fusion protein. The additional coding sequence can be provided within the assembled sequence in the case of synthetic genes. The production of a gene as a fusion protein can provide several benefits, including increased expression, greater stability, fast affinity purification using a support-bound ligand that binds to the additional polypeptide component, and cellular targeting of the gene product (for example, to a cell type possessing a cell surface receptor for the additional polypeptide component). Gene engineering incorporating this latter feature may be employed in the further development of gelonin-based therapeutics.

In the cloning and expression of DNA sequences encoding the plant toxin gelonin a wide variety of vectors are useful. These include, for example, vectors consisting of segments of chromosomal, non-chromosomal and synthetic DNA sequences, such as various known derivatives of SV40, known bacterial plasmids, (e.g.), plasmids from *E.coli* including col E1, pCR1, pBR322, pMB9 and their derivatives, wider host range plasmids, (e.g.), RP4, phage DNAs, (e.g.), the numerous derivatives of phage lambda, (e.g.), NM 989, and other DNA phages, (e.g.), M13 and filamentous single stranded DNA phages, yeast plasmids such as the 2 mu plasmid or derivatives thereof, and vectors derived from combinations of plasmids and phage DNAs, such as plasmids which have been modified to employ phage DNA or other expression control sequences.

Within each specific cloning or expression vehicle, various sites may be selected for insertion of the DNA sequences of this invention. These sites are usually designated by the restriction endonuclease which cuts them and are well recognized by those of skill in the art. Various methods for inserting DNA sequences into these sites to form recombinant DNA molecules are also well known. These include, for example, dG-dC or dA-dT tailing, direct ligation, synthetic linkers, exonuclease and polymerase-linked repair reactions followed by ligation, or extension of the DNA strand with DNA polymerase and an appropriate single-stranded template followed by ligation. It is, of course, to be understood that a cloning or expression vehicle useful in this invention need not have a restriction endonuclease site for insertion of the chosen DNA fragment. Instead, the vehicle could be joined to the fragment by alternative means.

For expression of the DNA sequences of this invention, these DNA sequences are operatively-linked to one or more expression control sequences in the expression vector. Such operative linking, which may be effected before or after the chosen DNA sequence is inserted into a cloning vehicle, enables the expression control sequences to control and promote the expression of the inserted DNA sequence.

Any of the wide variety of expression control sequences that control the expression of a DNA sequence may be used in these vectors to express the DNA sequence of this invention. Such useful expression control sequences, include, for example, the early and late promoters of SV40, the lac system, the trp system, the TAC or TRC system, the major operator and promoter regions of phase lambda, the control regions of fd coat protein, the promoter for 3-phosphoglycerate kinase or other glycolytic enzymes, the promoters of acid phosphatase, e.g., Pho5, the promoters of the yeast alpha-mating factors, and other sequences known to control the expression of genes of prokaryotic or eukaryotic cells or their viruses, and various combinations thereof. In mammalian cells, it is additionally possible to amplify the expression units by linking the gene to that coding for dehydrofolate reductase and applying a selection to host Chinese hamster ovary cells.

The vector or expression vehicle, and in particular the sites chosen therein for insertion of the selected DNA fragment and the expression control sequence employed in this invention are determined by a variety of factors. For example, these factors include the number of sites susceptable to a particular restriction enzyme, size of the protein to be expressed, expression characteristics such as the location of start and stop codons relative to the vector sequences. Other factors will be recognized by those of skill in the art. The choice of a vector, expression control sequence, and insertion site for a particular phospholipase inhibitor protein sequence is determined by a balance of these factors with not all selections being equally effective for a given case.

The recombinant DNA molecule containing the desired gene operatively linked to an expression control sequence may then be employed to transform a wide variety of appropriate hosts so as to permit such hosts (transformants) to express the gene, or fragment thereof, and to produce the polypeptide, or portion thereof, for which the hybrid DNA codes.

A wide variety of hosts are also useful in producing the antigens and DNA sequences of this invention. These hosts include, for example, bacteria, such as E.coli, Bacillus and Streptomyces, fungi, such as yeasts, and animal, such as CHO cells, and plant cells in tissue culture. The selection of an appropriate host is controlled by a number of factors recognized by the art. These include, for example, compatibility with the chosen vector, toxicity of the co-products, ease of recovery of the desired polypeptide, expression characteristics, biosafety and costs. No absolute choice of host maybe made for a particular recombinant DNA molecule or polypeptide from any of these factors alone. Instead, a balance of these factors must be struck with the realization that no all hosts may be equally effective for expression of a particular recombinant DNA molecule.

As we have previously demonstrated, it should be understood that the DNA sequences that are inserted at the selected site of a cloning or expression vehicle may include nucleotides which are not part of the actual gene coding for the desired polypeptide or may include only a fragment of the entire gene for that protein. It is only required that whatever DNA sequence is employed, the transformed host produces a protein gelonin or a polypeptide having substantially the same functional activity as gelonin. For example, the DNA sequences of this invention may be fused in the same reading frame in an expression vector to a portion of a DNA sequence coding for at least one eukaryotic or prokaryotic or prokaryotic carrier protein or a DNA sequence coding for at least one eukaryotic or prokaryotic signal sequence, or combinations thereof. Such constructions may aid in expression of the desired DNA sequence, improve purification or permit secretion, and preferably maturation, of the desired polypeptide from the host cell. The DNA sequence may alternatively include an ATG start codon, alone or together with other codons, fused directly to the sequence encoding the first amino acid of a desired polypeptide. Such constructions enable the production of, for example, a methionyl or other peptidyl polypeptide, that is part of this invention. This N-terminal methionine or peptide may then be cleaved intra- or extra-cellularly by a variety of known processes or the polypeptide used together with the methionine or other fusion attached to it in the compositions and methods of this invention.

EXAMPLES

Synthesis & Assembly of Gelonin Gene

Example 1

Binding of 5'-biotinylated oligonucleotide to streptavidin-coated latex microspheres A 0.2 ml sample of DYNABEADS M280 Streptavidin (Dynal Corp.) was placed into a 1.5 ml Eppendorf tube. The tube was held against a magnetic plate (Advanced Magnetics, Inc.) for a few minutes to cause the paramagnetic latex microspheres to be drawn to the side of the tube, then the fluid was drawn off. The beads were washed twice with 0.2 ml annealing buffer (composition given below) at room temp., then resuspended in 0.2 ml annealing buffer.

To the bead suspension was added 1 nmol of 5'-biotinylated oligonucleotide. After 30 min. at room temperature the beads were washed twice with 0.2 ml annealing buffer and resuspended in 0.2 ml annealing buffer. Spectrophotometric analysis of the unbound oligonucleotide in the washes indicated that approximately 300 pmol of oligonucleotide were bound to the beads.

Example 2

Annealing/washing cycle, repeated for addition of each successive oligonucleotide Before use in the gene assembly oligonucleotides were purified by polyacrylamide gel electrophoresis and enzymatically 5'-phosphorylated using T4 polynucleotide kinase.

To 150 pmol support-bound oligonucleotide were added 750 pmol overlapping complementary oligonucleotide and the annealing was carried out in 0.10 ml 50 mM sodium phosphate buffer, pH 7.5, 1M NaCl (annealing buffer) for 5 min. at 45 deg. C, then the mixture was cooled to room temperature over a 7 min. period. Beads were then washed twice with 0.2 ml of the same buffer at room temperature. This cycle was repeated until the last oligonucleotide in the assembly was added.

Example 3

Ligation of product and release from the support by restriction enzyme digestion After completion of the assembly the beads were washed and resuspended in 0.04 ml ligase buffer. After addition of 0.005 ml DNA ligase (New England Biolabs, high specific activity grade) the mixture was incubated at room temperature for 2 hours then washed and resuspended in 0.04 ml restriction digestion buffer. After addition of ten units of restriction endonuclease EcoRI the mixture was incubated at 37 degrees C for 90 minutes. The liquid was drawn off and the released DNA was ethanol precipitated and resuspended in 0.01 ml ligase buffer.

Example 4

Assembly of the gelonin gene

Figure 3:
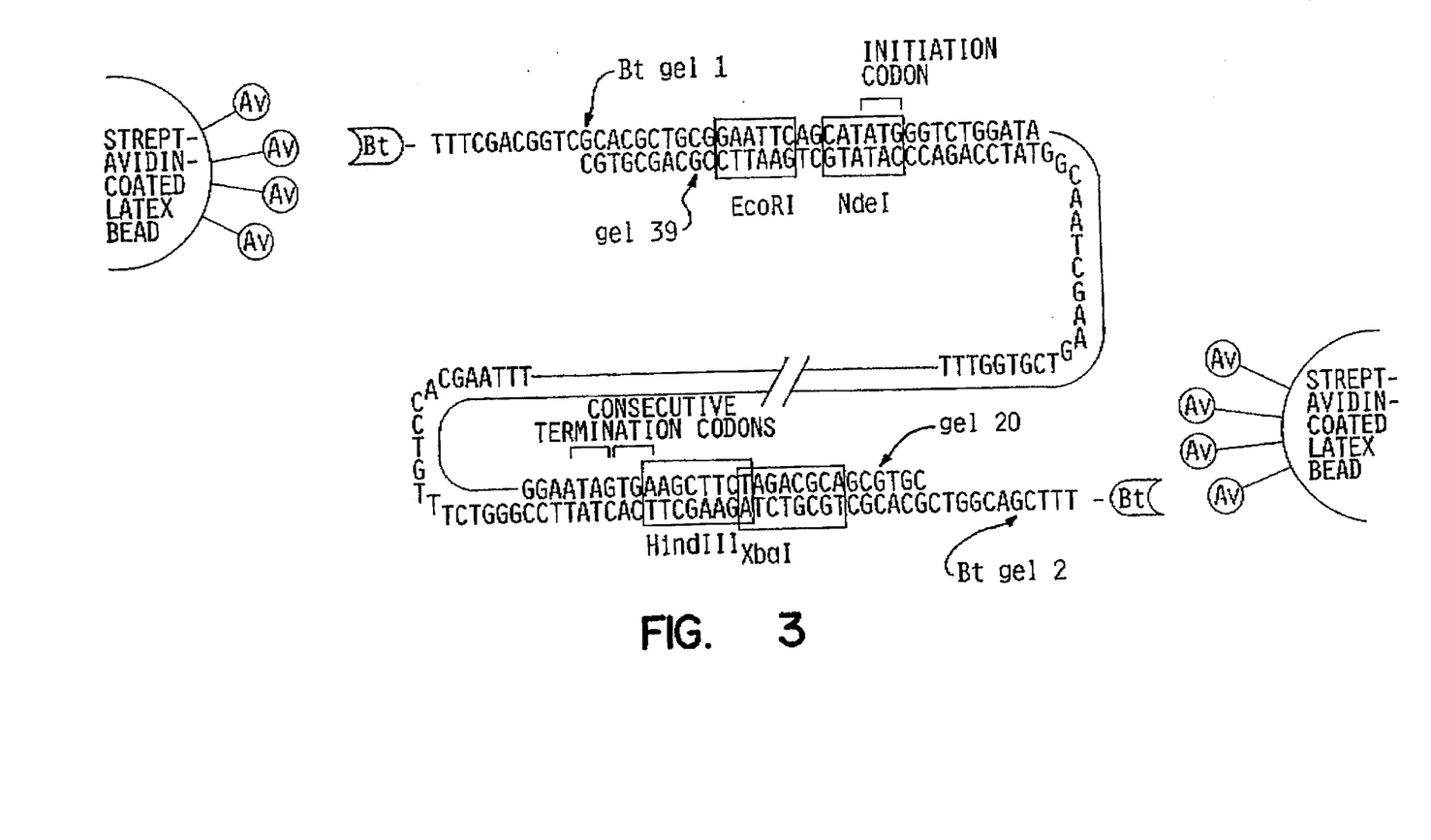
FIG. 3 illustrates a schematic diagram of the gelonin gene assembly process.
Figure 4:
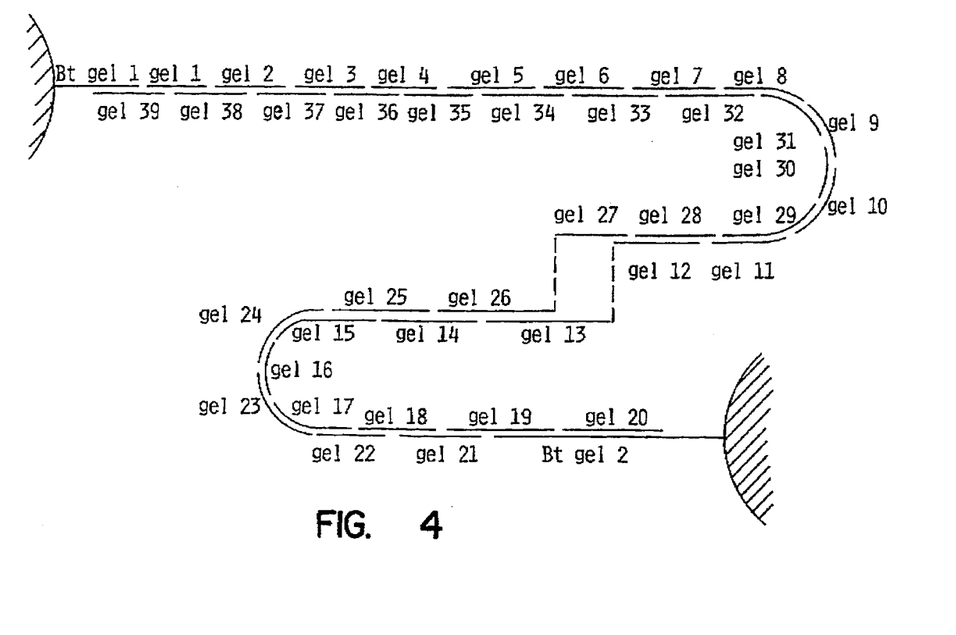
FIGS. 4 shows the schematic illustration of the arrangement of oligonucleotides in the gelonin gene assembly.

The gene was assembled from both directions as illustrated in FIG. 3 and FIG. 4. The oligonucleotide sequences are identified in FIG. 5. Assembly of the 5'-end of the gene (approximately 500 bp N-terminal coding region) began with support-bound Btge11 and the oligonucleotides were added in the following order (each involving one annealing/washing cycle): gel39, gel1, gel38, gel2, gel37, gel3, gel36, gel4, gel35, gel5, gel34, gel6, gel33, gel7, gel32, gel8, gel31, gel9, gel30, gel10, gel29, gel11, gel28, gel12, gel27.

Assembly of the 3'-end of the gene (approximately 300 bp C-terminal coding region) began with support-bound Btge12 and the oligonucleotides were added in the following order: gel20, gel19, gel21, gel18, gel22, gel17, gel23, gel16, gel24, gel15, gel25, gel14, gel26, gel13.

Referring to FIG. 3, the 5'-end of the gene (N-terminal coding region) was released from the support by digestion with restriction endonuclease EcoRI, and the 3'-end of the gene (C-terminal coding region) was released from the support by digestion with restriction endonuclease HindIII. Referring to FIG. 4, the two gene fragments, containing complementary 20-base tails within oligonucleotides gel27 and gel13, were annealed together, then ligated to form the intact gene.

Example 5

Cloning of the synthetic geloin gene

The completed DNA product was ligated with M13mp19RFDNA that had been cleaved with EcoRI and HindIII, according to standard methods described in Molecular Cloning: A laboratory manual, E. F. Sambrook et al., 1989.

Example 6

Sequencing of the synthetic gelonin gene

The sequence of the synthetic gene in M13mp19 was confirmed by dideoxy sequencing. Two mutations were found in the cloned synthetic gene, both in the 5'-end (N-terminal coding region).

Example 7

Site-directed mutagenesis to correct mutations in cloned synthetic gene

Oligonucleotide-directed mutagenesis was carried out to correct the two mutations within the gelonin gene, following the procedure supplied with the in vitro mutagenesis reagent kit (Amersham Corp.).

Example 8

Subcloning of synthetic gene into expression vector

The synthetic gelonin gene was cleaved from the M13mp19 vector by action of EcoRI and HINDIII and the gene-containing fragment was purified by agarose gel electrophoresis and ligated into EcoRI/HindIII-cleaved expression vector pKK223-3 (Pharmacia).

Example 9

Analysis of expression of synthetic gelonin gene in *E. coli*

A 50 ml culture of *E. coli* JM105 bearing the synthetic gelonin gene cloned into pKK223-3 is grown up, induced with IPTG and lysed to obtain a crude extract. The extract is analyzed by SDS polyacrylamide gel electrophoresis (along side a control extract prepared from host cells carrying the expression vector with no insert). Western blot analysis and functional assays of gelonin are also conducted to confirm that the protein is expressed and active.

In conclusion, therefore, it is seen that the present invention and the embodiments disclosed herein are well adapted to carry out the objectives and obtain the ends set forth at the outset. Certain changes can be made in the method and apparatus without parting from the spirit and scope of this invention. It is realized that changes are possible and it is further intended that each element or step recited in any of the following claims is to be understood as referring to all equivalent elements or steps for accomplishing substantially the same results in substantially the same or equivalent manner. It is intended to cover the invention broadly in whatever form its principles may be utilized. The present invention is therefore well adapted to carry out the objects and obtain the ends and advantages mentioned, as well as others inherent therein.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 783 base pairs
        ( B ) TYPE: nucleic acid
        ( C ) STRANDEDNESS: double
        ( D ) TOPOLOGY: unknown     ( i i ) MOLECULE TYPE: DNA (genomic)

( i i i ) HYPOTHETICAL: YES

( v i ) ORIGINAL SOURCE:
        ( A ) ORGANISM: Gelonium multiforum
        ( D ) DEVELOPMENTAL STAGE: Seed
        ( F ) TISSUE TYPE: Nut     ( x i ) SEQUENCE DESCRIPTION: SEQ ID NO:1:

```
ATGGGTCTGG  ATACCGTTAG  CTTCAGCACC  AAAGGCGCGA  CCTACATCAC  CTACGTTAAC          60
```

| | | | | | | |
|---|---|---|---|---|---|---|
| TTCCTGAACG | AACTGCGTGT | TAAACTGAAA | CCGGAAGGTA | ACAGCCATGG | CATCCCGCTG | 120 |
| CTGCGTAAAG | GTGATGACCC | GGGTAAATGC | TTCGTGCTGG | TGGCGCTGAG | CAACGATAAC | 180 |
| GGTCAGCTGG | CAGAAATCGC | AATCGATGTT | ACCAGCGTGT | ACGTAGTTGG | CTATCAGGTG | 240 |
| CGTAACCGCA | GCTACTTCTT | CAAAGATGCT | CCGGATGCAG | CGTACGAAGG | CCTGTTCAAA | 300 |
| AACACCATCA | AAACCCGCT | GCTGTTCGGT | GGCAAAACTC | GTCTGCACTT | CGGTGGCAGC | 360 |
| TATCCGAGCC | TGGAAGGCGA | AAAAGCGTAC | CGCGAAACTA | CCGATCTGGG | TATCGAACCG | 420 |
| CTGCGCATCG | GCATCAAAAA | ACTGGACGAA | AACGCGATCG | ACAACTACAA | ACCGACCGAA | 480 |
| ATCGCGAGCT | CTCTGCTGGT | TGTGATCCAG | ATGGTGAGCG | AAGCGGCACG | TTTCACCTTC | 540 |
| ATCGAAAACC | AGATTCGTAA | CAACTTCCAG | CAGCGTATCC | GTCCGGCGAA | CAACACCATC | 600 |
| TCTCTGGAAA | ACAAATGGGG | CAAACTGAGC | TTCCAGATCC | GTACCAGCGG | TGCGAACGGT | 660 |
| ATGTTCAGCG | AAGCGGTGGA | ACTGGAACGC | GCGAACGGCA | AAAATACTA | CGTGACTGCG | 720 |
| GTGGATCAGG | TGAAACCGAA | AATCGCACTG | CTGAAATTCG | TGGACAAAGA | CCCGGAATAG | 780 |
| TGA | | | | | | 783 |

What is claimed is:

1. A method of producing a synthetic gene encoding gelonin, comprising the steps of:
    selecting the sequence of a DNA fragment containing the sequence coding for gelonin, wherein said sequence contains a three base codon triplet for each amino acid in the gelonin sequence, said triplet is selected form the group of triplets coding for each amino acid to maximize expression, manipulation or stability of the DNA fragment in an expression vector synthesizing said fragment;

synthesizing the DNA fragment, wherein said synthesizing steps comprise:

dividing said DNA fragment into overlapping sets of single-stranded fragments of oligonucleotides, said fragments being chemically synthesized;

purifying said oligonucleotides;

phosphorylating said oligonucleotides on the 5' end;

annealing strands of oligonucleotides together, thus forming duplex DNA; thus forming a synthetic gene encoding gelonin.

2. The method of claim 1, wherein flanking sequences are attached to said duplex DNA.

3. A method of cloning the synthetic gene produced by the process of claim 1 into an expression vector, comprising the steps of:

(a) isolating the DNA encoding the gene in linear duplex form;

(b) cleaving an expression vector with a restriction endonuclease;

(c) joining said linear duplex DNA with said expression vector to form an expression vector containing said synthetic gene; and (d) transforming the DNA formed in step (c) into a host cell.

4. An expression vector comprising the synthetic gene produced by the process of claim 1.

5. A method of purifying the protein encoded by the synthetic gene produced by the process of claim 1, comprising the step of:

(a) cloning the gene into an expression vector;

(b) transforming said expression vector containing the gene into host cells, producing host cells containing the gone;

(c) growing the host cells containing the gene cloned into the expression vector, under conditions that induce the synthesis of the protein;

(d) purifying the protein from said cells.

6. The process of claim 1, wherein the condon triplets are selected to maximize expression in a suitable bacterial host.

7. The process of claim 1, wherein the condon triplets are selected to maximize expression in a suitable fungal host.

8. The process of claim 1, wherein the codon triplets are selected to maximize expression in mammalian cells.

9. The process of claim 1, wherein the codon triplets are selected to maximize expression in insect cells.

10. The process of claim 1, wherein the codons triplets are selected to maximize expression in plant cells.

11. The process of claim 1, wherein all of the oligonucleotides are annealed together in one reaction mixture to assemble the gene.

12. The process of claim 1, wherein the oligonucleotides are annealed in blocks and said blocks are subsequently annealed and ligated together to form the intact gene.

13. The process of claim 1, wherein the gene encoding gelonin is constructed by a solid phase assembly process comprising the steps of:

a. attaching a synthetic oligonucleotide at or near one end of said oligonucleotide to a solid phase support material;

b. washing away excess, unbound oligonucleotide;

c. adding a molar excess of oligonucleotide, which possesses perfect base sequence complementarity with the support-bound oligonucleotide, throughout part or all of said support-bound oligonucleotides, oligonucleotides length, and annealing the strands together to form a duplex DNA structure, then washing away excess, unbound oligonucleotide;

d. repeating step c until the entire gene has been assembled;

e. treating the assembled gene with DNA ligase to form an intact duplex DNA; and f. releasing the synthetic gene from the support with a restriction enzyme or other suitable means.

14. Synthetic DNA produced by the process of claim 1, containing a sequence of nucleotides coding for gelonin protein or for a polypeptide fragment of gelonin which inhibits cellular protein synthesis but does not bind to a cell surface receptor.

15. The method of claim 2, further comprising the incorporation of restriction endonuclease recognition sites into said synthetic gene or into a flanking sequence.

16. A method for verifying the sequence of the assembled and cloned gene of claim 4, further comprising the steps of:

(a) isolating vector DNA bearing the gene of claim 1;

(b) sequencing the gene-bearing vector DNA; and (c) repeating steps (a) and (b) with a multiplicity of clones until a clone containing the desired DNA sequence has been identified and the sequence of the assembled and cloned gene is verified.

17. A method for correcting by site-directed mutagenesis a mutation in the cloned gene of claim 6 which contains a mutation, comprising the steps of:

(a) isolating the DNA of said mutation-containing gene;

(b) annealing the DNA strand of the mutation-containing gene which contains the mutation with a synthetic corrective oligonucleotide primer spanning h site of said mutation and containing the correct DNA sequence;

(c) elongating the corrective oligonucleotide primer annealed to said mutation-containing strand by action of a DNA polymerase, producing a corrected gene;

(d) introducing the DNA product of step c into an appropriate host cell by transfection or transformation;

(e) isolating the corrected gene; and (f) subcloning the corrected gene into an expression vector.

18. The method of claim 5 further comprising the step of detecting the protein by SDS gel electrophoresis, Western blot analysis or activity assay.

19. The process of claim 7, wherein said host is *Escherichia coli*.

20. The process of claim 7, wherein the host is yeast.

21. The synthetic DNA of claim 14, wherein said nucleotide sequence is SEQ ID NO. 1.

22. An expression vector containing the DNA of claims 14 or 21.

23. The synthetic DNA of claim 21, wherein said nucleotide sequence is operatively linked to an expression control sequence.

24. The synthetic DNA of claim 21, further comprising a DNA sequence encoding a polypeptide domain that binds specifically to a cell surface receptor present on selected target cells.

25. The vector of claim 22, wherein said vector is pKK223-3.

26. A host cell containing and expressing the expression vector of claim 22.

27. The host cell of claim 26 wherein said host cell is selected from the group consisting of bacteria, fungi, insect cells, animal cells and plant cells.

28. The host cell of claim 26 wherein said host cell is selected from the group consisting of mouse, swine, and human tissue cells.

29. The host cell of claim 26, wherein said host cell is selected from the group consisting of strains of *E. coli*, Pseudomonas, Bacillus and yeast.

30. The synthetic DNA of claim 23, wherein said expression control sequence is selected from the group consisting of an early promoter of SV40, a late promotor of SV40, a loc system, a TAC system, a TRC system, a TRP system, major operator and promotor regions of lambda and control regions of fd coat protein.

31. The host cell of claim 29, wherein the *E. coli* is *E. coli* JM105.

32. A process of producing the synthetic DNA sequence of SEQ ID NO:1 comprising:

a. synthesizing, purifying and 5'-phosphorylating a set of synthetic oligonucleotides which when linked together make the synthetic gene; and b. annealing and ligating the oligonucleotides together to assemble the synthetic gene.

33. A process for producing, cloning and expressing a synthetic gene encoding gelonin, comprising the steps of:

a. selecting the sequence of a double-stranded DNA fragment containing a sequence of three base codons corresponding to the primary amino acid sequence determined from purified gelonin protein so that said DNA sequence has features that facilitate synthesis, cloning, expression or biochemical manipulation of the gene;

b. designing, synthesizing, purifying and 5'-phosphorylating a set of synthetic oligonucleotides which when linked together to make the synthetic gene;

c. annealing and ligating the oligonucleotides together to assemble the synthetic gene;

d. ligating the synthetic gene together with a suitable cloning vector;

e. determining the nucleotide sequence of the cloned gene to verify the sequence of the gene;

f. conducting site-directed mutagenesis to correct any undesired mutations in the cloned gene;

g. subcloning the gene into an expression vector;

h. introducing the expression vector bearing the synthetic encoding gelonin into an expression host cell, and i. growing the host cell bearing the expression vector of step (h) under conditions suitable for production of the gelonin product.

* * * * *

UNITED STATES PATENT AND TRADEMARK OFFICE
CERTIFICATE OF CORRECTION

PATENT NO. : 5,624,827
DATED : Apr. 29, 1997
INVENTOR(S) : Michael G. Rosenblum, et al It is certified that error appears in the above-identified patent and that said Letters Patent is hereby corrected as shown below:

In Column 1, line 10, after the word "process", the words --for the production-- should be inserted.

In Column 1, line 21, "ribosoms" should read --ribosomes--.

In Column 1, line 24, "Barbibieri" should read --Barbieri--.

In Column 5, line 26, "wavers" should read --wafers--.

In Column 7, line 1, "phase" should read --phage--.

In Column 7, line 42, "maybe" should read --may be--.

In Column 7, line 45, "no" should read --not--.

In Column 10, line 10, "HINDIII" should read --HindIII--.

In Column 11, line 32 (Claim 1), "form" should read --from--.

UNITED STATES PATENT AND TRADEMARK OFFICE
CERTIFICATE OF CORRECTION

PATENT NO. : 5,624,827
DATED : Apr. 29, 1997
INVENTOR(S) : Michael G. Rosenblum, et al It is certified that error appears in the above-identified patent and that said Letters Patent is hereby corrected as shown below:

In Column 11, line 66 (Claim 5), "step" should read --steps--.

In Column 12, line 28 (Claim 5), "gone" should read --gene--.

In Column 12, line 33 (Claim 6), "condon" should read --codon--.

In Column 12, line 35 (Claim 7), "condon" should read --codon--.

In Column 12, line 41 (Claim 10), "codons" should read --codon--.

In Column 12, line 60 (Claim 13), "oligonucleotides," (first occurrence) should be deleted.

In Column 12, line 61 (Claim 13), "strands" should be replaced with --oligonucleotides--.

In Column 13, line 21 (Claim17), "claim 6" should read --claim 4--.

In Column 13, line 26 (Claim 17), "h" should read --the--.

UNITED STATES PATENT AND TRADEMARK OFFICE
CERTIFICATE OF CORRECTION

PATENT NO. : 5,624,827
DATED : Apr. 29, 1997
INVENTOR(S) : Michael G. Rosenblum, et al It is certified that error appears in the above-identified patent and that said Letters Patent is hereby corrected as shown below:

In Column 13, line 30 (Claim 17), after the words "mutation-containing", the word --DNA-- should be inserted.

In Column 13, line 41 (Claim 19), "claim 7" should read --claim 6--.

In Column 14, line 11 (Claim 29), "Pseudomonas, Bacillus" should read --*Pseudomonas, Bacillus*--.

In Column 14, line 16 (Claim 30), prior to the word "lambda", the word --phage-- should be inserted.

In Column 14, line 39 (Claim 33), please delete the word "to".
In Column 14, line 49 (Claim 33), after the word "synthetic", the word --gene-- should be inserted.

Signed and Sealed this

Sixth Day of October, 1998

Attest:

BRUCE LEHMAN

*Attesting Officer*   *Commissioner of Patents and Trademarks*